United States Patent [19]

Seko et al.

[11] Patent Number: 4,611,199
[45] Date of Patent: Sep. 9, 1986

[54] ALARM SYSTEM AND METHOD FOR SENSING A STAND-BY STATE IN A DRIVER DROWSINESS DETECTION SYSTEM

[75] Inventors: Yasutoshi Seko, Yokohama; Haruhiko Iizuka; Takayuki Yanagishima, both of Yokosuka; Hideo Obara, Yokosuka, all of Japan

[73] Assignee: Nissan Motor Company, Yokohama, Japan

[21] Appl. No.: 580,177

[22] Filed: Feb. 15, 1984

[30] Foreign Application Priority Data

Feb. 18, 1983 [JP] Japan ................... 58-24849

[51] Int. Cl.⁴ .......................................... G08B 23/00
[52] U.S. Cl. ..................... 340/576; 180/272
[58] Field of Search ............... 340/575, 576, 52 D, 340/52 R; 180/272

[56] References Cited

U.S. PATENT DOCUMENTS

| | | | |
|---|---|---|---|
| 3,106,981 | 10/1963 | Chakiris | 180/272 |
| 3,222,639 | 10/1965 | Kayser, Jr. | 340/576 X |
| 3,654,599 | 4/1972 | Sepper | 340/576 X |
| 3,794,969 | 2/1974 | Klopfenstein | 340/576 X |
| 3,877,541 | 4/1975 | Takeuchi et al. | 340/576 X |
| 3,938,612 | 2/1976 | Boudeville et al. | 180/197 |
| 3,980,999 | 9/1976 | Nishioka et al. | 340/56 |
| 4,005,398 | 1/1977 | Inoue et al. | 340/576 X |
| 4,007,357 | 2/1977 | Yanagishima | 377/45 |
| 4,017,843 | 4/1977 | Yanagishima | 340/576 |
| 4,031,527 | 6/1977 | Yanagishima et al. | 340/576 X |
| 4,058,796 | 11/1977 | Oishi et al. | 340/575 X |
| 4,104,621 | 8/1978 | Yanagishima et al. | 340/576 |
| 4,224,609 | 9/1980 | Yanagishima et al. | 340/576 |
| 4,278,969 | 7/1981 | Woods | 340/576 |
| 4,463,347 | 7/1984 | Seko et al. | 340/576 |
| 4,476,938 | 1/1985 | Seko et al. | 340/576 |

FOREIGN PATENT DOCUMENTS

| | | |
|---|---|---|
| 0060306 | 4/1982 | European Pat. Off. |
| 2042853 | 3/1972 | Fed. Rep. of Germany |
| 2509354 | 8/1977 | Fed. Rep. of Germany |
| 55-121732 | of 0000 | Japan |
| 55-156725 | of 0000 | Japan |
| 56-73638 | of 0000 | Japan |
| 56-2225 | of 0000 | Japan |
| 56-2226 | of 0000 | Japan |

*Primary Examiner*—James L. Rowland
*Assistant Examiner*—Jeffery A. Hofsass
*Attorney, Agent, or Firm*—Lowe, Price, Leblanc Becker & Shur

[57] ABSTRACT

A drowsiness alarm system and method for use in automotive vehicles is set to a stand-by state in response to a specific sequence of steering wheel maneuvers which may reflect driver drowsiness, for example, a relatively long period during which the steering wheel is not turned followed by an abrupt steering adjustment. From the standby state, an alarm or display alerting the driver will be generated in response to another sequence of steering maneuver confirming driver drowsiness. The second sequence of maneuvers may be selected from among a number of conventional steering behavior criteria. If driver drowsiness is not confirmed within a predetermined period of time after initiation of the stand-by state, the system is reset to its initial state.

24 Claims, 9 Drawing Figures

ALARM SYSTEM AND METHOD FOR SENSING A STAND-BY STATE IN A DRIVER DROWSINESS DETECTION SYSTEM

BACKGROUND OF THE INVENTION

The present invention relates to an alarm system and method for detecting drowsiness of an automotive vehicle driver and delivering an alarm to keep the driver awake or, in turn, to recommend to the driver to take a rest in the interest of safety. More particularly, the present invention relates to a drowsiness alarm system for an automotive vehicle driver which detects drowsiness by way of observation of the driver's steering behavior.

During relatively long driving periods, for example, long-distance highway cruising, a vehicle driver is apt to face drowsiness at the wheel. If the vehicle driver dozes or feels intensely drowsy, driving behavior distinct from normal waking conditions will occur. Therefore, driver drowsiness can be detected by detecting such abnormal driving behavior.

Various approaches have been proposed in pursuit of reliable recognition of steering behavior due to driver drowsiness.

For example, the co-pending U.S. patent application Ser. No. 304,254, filed on Sept. 21, 1981, now U.S. Pat. No. 4,463,347, the corresponding European patent application of which has been published as Published European patent application No. 0048492, discloses a drowsiness alarm system which detects quick or abrupt steering operations and produces an alarm in response to the number of abnormally abrupt steering operations exceeding a predetermined value.

The Published European patent application No. 0049522 discloses a drowsiness alarm system for a vehicle which delivers an alarm to the vehicle driver to prevent driving in an increasing state of drowsiness. According to that invention, a drowsiness alarm system comprises a steering angle pulse generation circuit which produces first and second angle pulses whenever the steering wheel is rotated clockwise and counter-clockwise, respectively, through a predetermined angular increment, a curved road detection circuit, responsive to the first and second steering pulses, which counts the number of the first and second steering pulses separately and judges that the vehicle is travelling on a curved road when the counted number of either of the first and second steering pulses reaches a first predetermined number within a predetermined period of time or when the difference between the counted numbers of the first and second steering angle pulses reaches a second predetermined number within the predetermined period of time, a first counting circuit which counts the number of the first and second steering angle pulses within the predetermined period of time and outputs a first alarm signal whenever the counted number reaches a third predetermined number, a second counting circuit responsive to the curved road detection circuit which counts the number of the first and second steering angle pulses and outputs a second alarm signal whenever the counted number reaches a fourth predetermined number greater than the third predetermined number, and an alarm unit which delivers an alarm to the driver in response to the first and second alarm signal.

The co-pending U.S. patent application Ser. No. 326,392, now U.S. Pat. No. 4,496,938, the Japanese counterpart of which has been published as the Published Japanese Pat. No. 56-2226, discloses a drowsiness alarm system for a vehicle which detects the driver's increasing state of drowsiness on the basis of abnormal steering change repetitions for a fixed period of time in a monotonous driving state defined, for example, by the gear shift lever being in the overdrive or top position. The alarm system produces an alarm to the driver to prevent the driver from allowing himself to become more drowsy. The drowsiness alarm system disclosed therein comprises: (a) a steering signal generator which generates a signal corresponding to the angle through which the steering wheel is rotated; (b) a monotonous driving-state detector which detects and signals that the vehicle is travelling in a monotonous driving state; (c) a discriminator which compares the change of steering signal level from said steering signal generator with a reference value for a fixed period of time; and (d) an alarm pulse generator which outputs an alarm pulse into an alarm circuit producing an alarm in response to the input alarm pulse when the output signal from the discriminator indicates that the change of steering signal exceeds the reference voltage throughout the fixed period of time.

The co-pending U.S. patent application Ser. No. 326,393, the Japanese counterpart of which has been published as Published Japanese Pat. No. 56-2225, discloses an alarm system for a vehicle driver to prevent same from dozing at the wheel. The system includes means for detecting driver drowsiness on the basis of abnormal steering change repetitions for a fixed period of time in a monotonous driving state defined, for example, by the transmission being maintained at an overdrive or top gear. The alarm system produces an alarm to the driver to prevent the driver from allowing himself to become more drowsy. The drowsiness alarm system disclosed therein comprises a steering signal generator which generates a signal corresponding to the angle through which the steering wheel is rotated, a monotonous driving-state detector which detects and signals that the vehicle is travelling in a monotonous driving state, a discriminator which compares the change of steering signal level from said steering signal generator for a fixed period of time with a reference value, and an alarm pulse generator which sends an alarm pulse to an alarm circuit producing an alarm in response to the input alarm pulse when the output signal from the discriminator indicates that the change of steering signal exceeds the reference voltage throughout the fixed period of time.

The Published European patent application No. 0059225 discloses a warning device for a vehicle which comprises a steering angle detector producing steering angle pulses indicative of the steering angle and the steering direction whenever the variation of the steering angular position exceeds a predetermined angle, a dozing detecting circuit which recognizes that the driver is alert when relatively frequent steering operations in one direction are performed and that the driver is dozing when steering adjustments which do not exceed the predetermined angle in one direction are repeated at a rate greater than a predetermined frequency in which case it outputs a warning signal, and a warning means for producing a visible or audible warning in response to the warning signal, whereby the warning device can accurately detect dozing of the driver and produce a warning to make the driver wake up.

The Published European patent application No. 0060306 discloses a warning device which detects abrupt steering when the driver is dozing at the wheel and in such cases, delivers a warning. The warning device comprises a sensor for detecting steering variation angle, a circuit for detecting abrupt steering based on detected right- and left-hand steering angle variations, and circuits for operating a warning means when consecutive abrupt steering adjustments to the left and to the right are detected within a given period.

The Published European patent application No. 0061501 discloses a warning device for a vehicle which comprises a steering angle detector producing steering angle pulses indicative of the steering angle and the steering direction whenever the variation of the steering angular position exceeds a predetermined angle, a dozing detecting circuit which recognizes that the driver is alert when relatively frequent steering operations in one direction are performed or when the interval between consecutive steering angle pulses is longer than a predetermined value, and producing a warning signal when steering adjustments which do not exceed the predetermined angle in one direction are repeated at a rate greater than a predetermined frequency, and a warning means for producing a visible or audible warning in response to the warning signal, whereby, the warning device can accurately detect dozing of the driver and produce a warning to make the driver wake up.

The Published European patent application No. 0061500 discloses a doze warning system which includes a circuit for producing a pulse signal representative of left- and right-hand steering adjustments, a circuit which counts the pulses of the pulse signal and produces a warning signal when the counter valve reaches a threshold value, and a circuit for producing a reset signal to clear the counter value when a difference between the number of pulse signals representative of left-hand steering adjustment and of right-hand steering adjustment exceeds a given value, or one of the left-hand or right-hand pulse signal counts exceeds a predetermined pulse number. The reset signal generating circuit detects steering adjustments exceeding the threshold value under normal driving conditions such as travelling along a curved road and produces the reset signal to inhibit production of this warning. By this reset signal generating circuit function, the warning system is prevented from malfunctioning.

The present invention intends to provide a drowsiness alarm system which can detect driver drowsiness more precisely and satisfactorily while eliminating occurrences of mis-judgment.

SUMMARY OF THE INVENTION

Therefore, it is an object of the present invention to provide a drowsiness alarm system for an automotive vehicle driver which is capable of detecting two distinctive steering behavior stages.

Another and more specific object of the invention is to provide a drowsiness alarm system which detects periods wholly lacking in steering adjustments, the duration of which exceeds that possible under normal alert conditions and detects specific steering behavior reflecting driver drowsiness.

In order to accomplish the above-mentioned and other objects, an alarm system for a dozy driver detects cessation of steering operations for a period longer than an assumed normal length and a subsequent abrupt steering adjustment in one direction through at least a predetermined angle. When cessation of steering for a period longer than the assumed length and the subsequent abrupt steering adjustment are both detected, the alarm system is switched to stand-by condition in which it produces an alarm when a predetermined steering adjustment satisfying an alarm condition is subsequently detected.

According to one aspect of said invention, an alarm system for a drowsy vehicle driver comprises a first detector for measuring a first period of time in which vehicle steering is substantially absent, said first detector being responsive to a first period of time longer than a first threshold to produce a first detector signal, a second detector for detecting a steering adjustment in a single direction, said second detector being responsive to steering adjustments through an angle exceeding a second threshold in said presence of said first detector signal to switch said alarm system to a stand-by state, a third detector for detecting a preselected steering operational condition while said system is in said stand-by state, and producing an alarm signal in response thereto, and an alarm means responsive to said alarm signal to produce an alarm to keep said driver awake.

According to another aspect of said invention, an alarm system for notifying a vehicle driver of drowsiness comprises a first sensor for detecting steering adjustments and producing a sensor pulse whenever said steering wheel angular position is adjusted through a given unit angle, said sensor signal being indicative of said direction in which said steering adjustment occurs, a second detector for measuring said period of time between consecutive sensor pulses and producing a second signal indicative of said measured period of time, a third detector responsive to said second signals having a value exceeding a first threshold to produce a third signal, a fourth detector for counting said first signals indicative of steering adjustment in said same direction and separated in time by less than a second threshold, said fourth detector producing a fourth signal to switch said system to a standby state when its counter value exceeds a third threshold, a fifth detector for detecting a steering operation satisfying a predetermined alarm condition in said presence of said fourth signal to produce an alarm signal, and an alarm means, responsive to said alarm signal, for producing an alarm to keep said vehicle driver awake.

According to a further aspect of said invention, an alarm system for a vehicle driver for producing an alarm in order to prevent said driver from dozing at said wheel, comprises a first detector detecting steering adjustments through an angle exceeding a first threshold and producing a first signal when said steering adjustment is performed in a first direction and a second signal when said steering adjustment is performed in a second direction opposite said first direction, said first detector producing one of said first and second signals whenever said angle of adjustment of said steering wheel exceeds said first threshold, a second detector receiving said first and second signals, measuring said intervals between consecutive first and/or second signals to produce an interval-indicative signal indicative of said measured intervals, a third detector which produces a third signal when said interval-indicative signal value exceeds a second threshold, a fourth detector responsive to said interval-indicative signal value being less than a third threshold to count occurrences of one of said first and second signals as long as said intervals between consecutive occurrences of said one of said first and second signals remain less than said third threshold, said fourth detector comparing its counter value with a fourth threshold and producing a fourth signal when said counter value exceeds said fourth threshold in said presence of said third signal, a fifth detector which produces an alarm signal when a steering operational condition satisfies a predetermined alarm condition in said presence of said fourth signal, and means for producing an alarm in response to said alarm signal.

According to a still further aspect of the invention, a method for detecting the drowsiness of a vehicle driver comprises the steps of detecting occurrences of steering adjustments to detect intervals between occurrences exceeding a first given threshold, detecting occurrences of steering adjustments through angles exceeding a second threshold within a given period of time after the occurrence of intervals exceeding the first given threshold, detecting a specific steering operation within a period of time less than a third threshold after the occurrence of steering adjustments exceeding the second threshold, and producing an alarm in response to the specific steering operation occurring after the steering adjustment exceeding the second threshold.

BRIEF DESCRIPTION OF THE DRAWINGS

The present invention will be understood more fully from the detailed description given below and from the accompanying drawings of the preferred embodiment of the present invention, which should not be taken to limit the invention but are for explanation and understanding only.

In the drawings.

DESCRIPTION OF THE PREFERRED EMBODIMENTS

Figure 1:
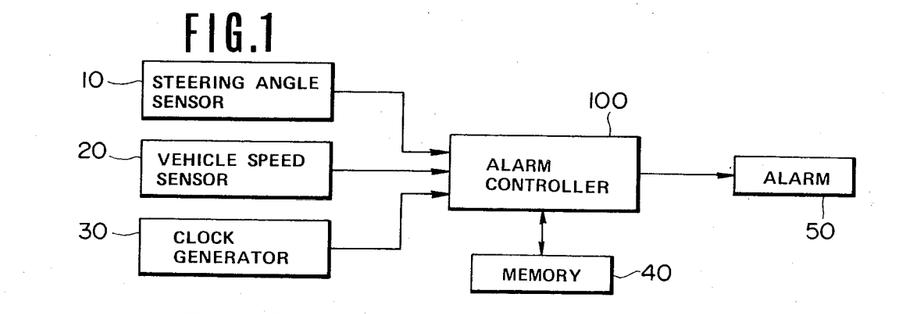
FIG. 1 is a schematic block diagram of the general structure of the preferred embodiment of a drowsiness alarm system according to the present invention.

Referring now to the drawings, particularly to FIG. 1, the preferred embodiment of a drowsiness alarm system according to the present invention includes an alarm controller 100 detecting a predetermined or preselected alarm condition and producing an alarm signal to activate an alarm unit 50 connected thereto.

The alarm controller 100 receives a sensor signal in the form of a pulse train from a steering angle sensor 10. The phase of sensor signal pulses vary in accordance with the steering direction. Therefore, by detecting the signal phase, the steering direction can be detected. The alarm controller 100 is also connected to a vehicle speed sensor 20 detecting vehicle speed and producing a vehicle speed-indicative signal having a value proportional to or representative of the vehicle speed. A clock generator 30 is also connected to the alarm controller 100 to supply clock signals.

The alarm controller is further associated with a memory 40 for recording the times at which the steering angle sensor signals are received. Based on the stored time data in the memory, and the magnitude of steering angular adjustments derived by counting the steering angle sensor signals in each direction, the alarm controller detects a specific pattern of steering behavior which appears when the driver is dozing at the wheel and produces an alarm to keep the driver awake. Furthermore, the alarm controller 100 takes the vehicle speed-indicative signal value into account by inhibitting detection of the preselected alarm condition when the vehicle speed is less than a given speed.

Figure 3:
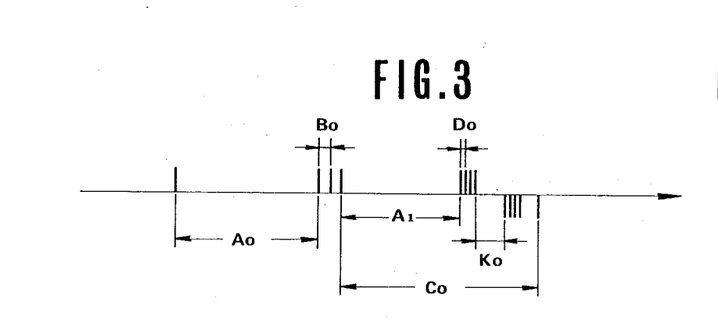
FIG. 3 is a timing chart of sensor pulses which may occur when a driver dozes at the wheel.

The specific alarm conditions sought in the preferred embodiment will be explained with reference to FIG. 3. As will be appreciated from FIG. 3, the specific steering adjustment pattern in response to which to produce an alarm consists of two sequential, distinct steering adjustments. At first, the alarm controller 100 detects a period of time during which no steering adjustments take place, which will be referred to hereafter as "monotonous state" and the duration of the monotonous state will be referred to hereafter as "monotonous state period". When a steering adjustment exceeding a given angle occurs subsequent to a monotonous state which exceeds a given period of time, the alarm controller is to produce an alarm signal when a predetermined second steering adjustment is detected thereafter. This state in which the alarm controller can be triggered by the second steering adjustment to produce the alarm signal will be referred to hereafter as "stand-by state". The steering adjustment to be detected after the alarm controller enters the "stand-by state", referred to hereafter as "alarm condition", can be selected from any of the steering operational states detected by the systems disclosed in the co-pending U.S. patent applications Ser. Nos. 304,254 (corresponding to EPO Publication No. 0048492), 309,012 (corresponding to EPO Publication No. 0049522), 326,392 (corresponding to Published Japanese Pat. No. 56-2225), 326,393 (corresponding to Published Japanese Pat. No. 56-2226), 377,267 (corresponding to the EPO Publication No. 0059225), 377,268 (corresponding to the EPO Publication No. 0060306), 377,198 (corresponding to the EPO Publication No. 0061501), and 377,206 (corresponding to the EPO Publication No. 0061500). The disclosure of the above-identified co-pending applications and publications are hereby incorporated by reference for the sake of disclosure.

In the shown embodiment, the alarm controller 100 detects abrupt steering adjustment exceeding a predetermined angle in both opposing directions as the alarm condition. In the preferred procedure, the alarm controller detects monotonous states occurring after initiation of the stand-by state and subsequent consecutive abrupt steering adjustments in opposite directions produce the alarm signal.

Figure 2:
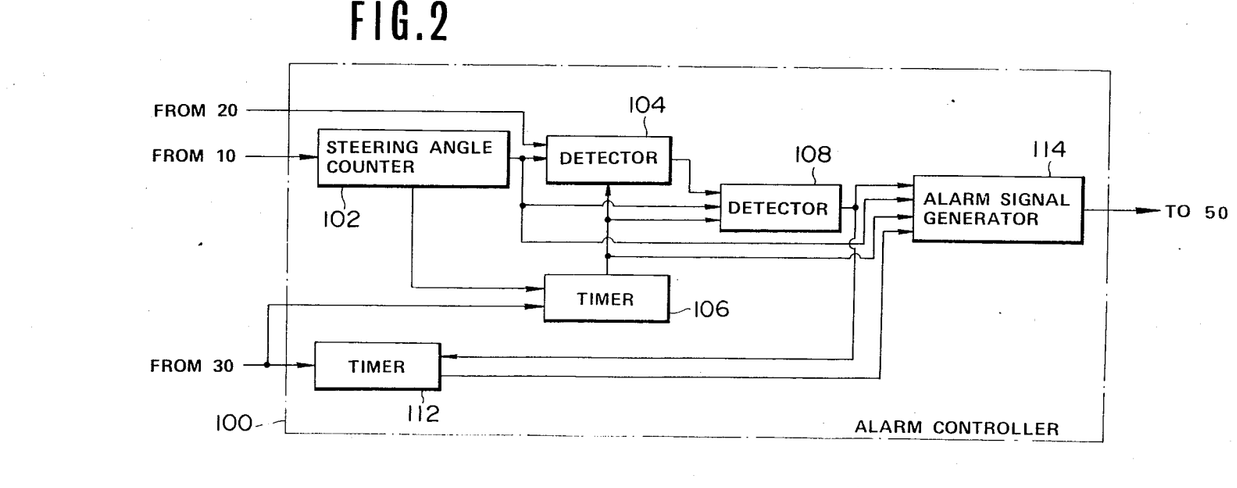
FIG. 2 is a block diagram of an alarm controller in the drowsiness alarm system of FIG. 1.
Figure 4:
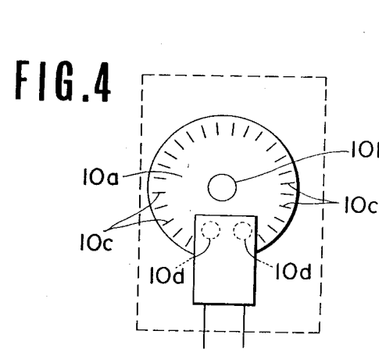
FIG. 4 is an illustration of a steering angle sensor.

The detailed structure and function of the aforementioned alarm controller 100 will be described with reference to FIG. 2. In FIG. 2, a steering pulse generator 102 is connected to the steering angle sensor 10 to receive the sensor signals. As shown in FIG. 4, the steering angle sensor 10 comprises a rotary disc 10a fixed to a steering column 10b for rotation therewith. The rotary disc 10a has a plurality of slits 10c arranged symmetrically about its circumference. The slits are separated by equal angular intervals and all have the same width. In the shown embodiment, both the width of the slits and the edge-to-edge separation therebetween are about 2°, which is defined as the unit of steering adjustment. A pair of photoelectric sensor elements 10d are arranged to be so separated relative to the arrangement of the slits that rotation of the steering wheel in different directions produces different sequences of pulse-combination changes. The detailed arrangement thereof has been disclosed in the co-pending Japanese Pat. No. 58-24605. The disclosure of the above-identified Japanese Patent concerning the steering angle is hereby incorporated by reference for the sake of disclosure.

The steering pulse generator 102 distinguishes changes in the combinations specifying one direction of steering operation from changes in the combinations specifying the other direction of steering operation. The steering pulse generator 102 produces a steering pulse, the phase of which represents the steering direction. For example, when left-hand steering is detected, the steering pulse generator produces a positive-phase steering pulse per each unit angle of steering adjustment and when right-hand steering is detected, the steering pulse generator produces a negative-phase steering pulse per each unit of steering adjustment.

The steering pulse generator 102 sends the steering pulse representative of the steering direction and indicative of a unit angle of steering adjustment to a first detector 104. The first detector 104 is connected to a first timer 106 adapted to count the clock signal pulses from the clock generator 30. The first timer 106 is, in turn, connected to the steering pulse generator 102 to be reset and restarted in response to each steering pulse. The first detector 104 receives a first timer signal having a value indicative of the counted value of the first timer 106. The first detector 104 is responsive to timer signals having a value larger than a predetermined value $A_0$, which predetermined period of time will be referred to hereafter as "first monotonous threshold $A_0$", to produce a first detector signal. The presence of the first detector signal indicates steering behavior corresponding to the monotonous state for a period of time longer than the monotonous threshold $A_0$, e.g. 3 sec.

On the other hand, the first timer 106 is responsive to each steering pulse from the steering pulse generator 102 to be reset to zero. The first detector 104 is connected to the vehicle speed sensor 20 to receive a vehicle speed signal having a value proportional to the vehicle speed. The first detector 104 compares the vehicle speed signal value with a given speed threshold indicative of a predetermined minimum vehicle speed e.g. 50 km/h, to enable the alarm controller 100. When the vehicle speed signal value is less than the given speed threshold, the first detector 104 is inhibitted from detecting the timer signal or producing the first detector signal. Therefore, the first detector 104 is operative only while the vehicle speed is held above the predetermined minimum speed.

The first detector signal is fed to a second detector 108 which is adapted to detect steering adjustments exceeding a predetermined angle in one direction to produce a second detector signal. To detect the unidirectional steering adjustment, the second detector 108 counts steering pulses having the same phase. The counter value of the second detector 108 is cleared when a steering pulse of the opposite phase, which is representative of the other direction of steering, is received. The second detector 108 is further connected to the first timer to receive the first timer signal indicative of the intervals between consecutive steering pulses to be counted. As long as the first timer signal value remains less than a given value $B_0$ which is representative of a given pulse interval, referred to hereafter as "first timer threshold $B_0$", the second detector 108 continues to count the steering pulses. The second detector 108 compares its counter value with a reference value and produces a second detector signal which switches the alarm controller to the stand-by state. The second detector signal is fed to an alarm signal generator 114 and a second timer 112. The second timer 112 is responsive to the second detector signal to start counting the clock signal pulses from the clock signal generator 30 and to output a second timer signal sequentially.

The second timer signal of the second timer 112 is supplied to the alarm signal generator 114. The alarm signal generator 114 is also connected to the first timer 106 to receive therefrom the first timer signal indicative of the steering pulse interval. The alarm signal generator 114 detects monotonous state occurring in the presence of the second detector signal and measures duration of the monotonous state which will be longer than a second monotonous threshold $A_1$. The alarm signal generator 114 will then output an alarm signal if a series of steering angle pulses in one direction exceeding a predetermined number subsequent to the monotonous state and having pulse intervals shorter than a second timer threshold $D_0$ and a series of steering pulse representative of steering in the opposite direction with pulse interval shorter than the second timer threshold and occurring within a period of time $K_0$ after termination of the first-mentioned series of steering pulses are both received.

The conditions under which the alarm signal generator 114 will produce the alarm signal are as follows in the illustrated embodiment:
  presence of the second detector signal;
  a monotonous state longer than the second monotonous threshold $A_1$;
  more than a given number of steering pulses indicative of a first direction of steering adjustment, each of the steering pulses following the preceding pulse by less than $D_0$; and
  more than a given number of steering pulses indicative of the opposite direction of steering adjustment, each of the steering pulses following the preceding pulses by less than $D_0$, and the first of which is received within a period of time $K_0$ of the last of the pulses in the first direction.

If any of the foregoing conditions are not satisfied, the alarm signal generator 114 will output a reset signal to the second detector to reset the latter to its initial state signal generator 114 in response to the second timer signal having a value more than a given period of time $C_0$.

Figure 5:
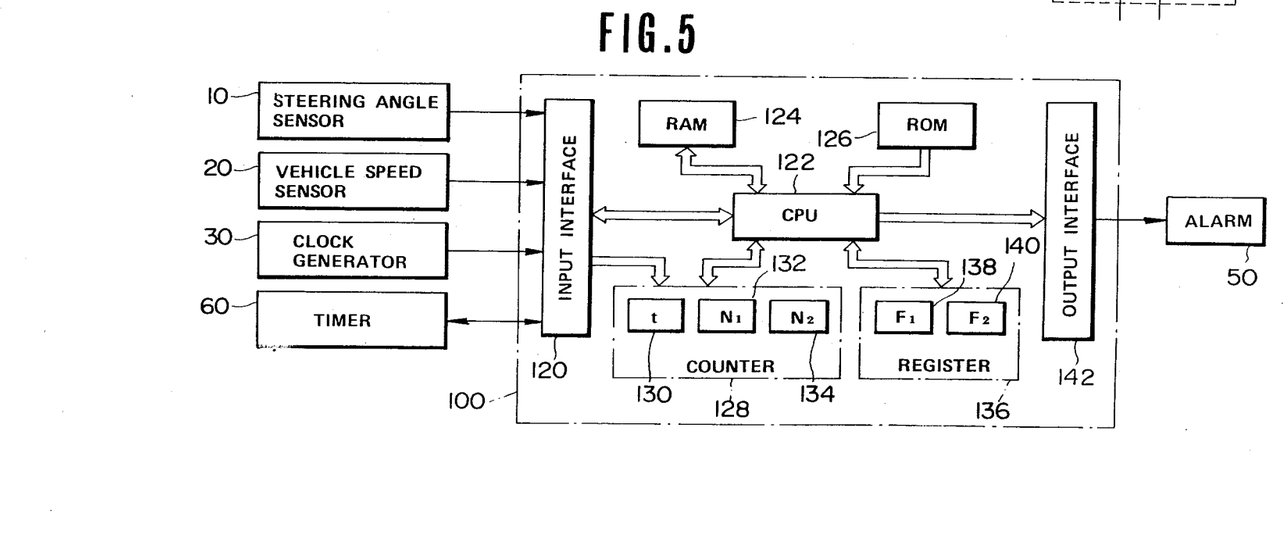
FIG. 5 is a block diagram of a modification of the drowsiness alarm system according to the present invention.

Referring to FIG. 5, the second embodiment of the drowsiness alarm system includes an alarm controller 100' comprising a microcomputer or microprocessor. As is well known, the microprocessor acting as the alarm controller includes an input interface 120, CPU 122, RAM 124, ROM 126 and an output interface 142. The microprocessor further comprises a counter 128 and a register 130. The counter includes section 130, 132 and 134 adapted to count the clock signal pulses and the steering angle pulses. The register 130 includes memory sections 138 and 140 which serve to hold flags.

Figure 6:
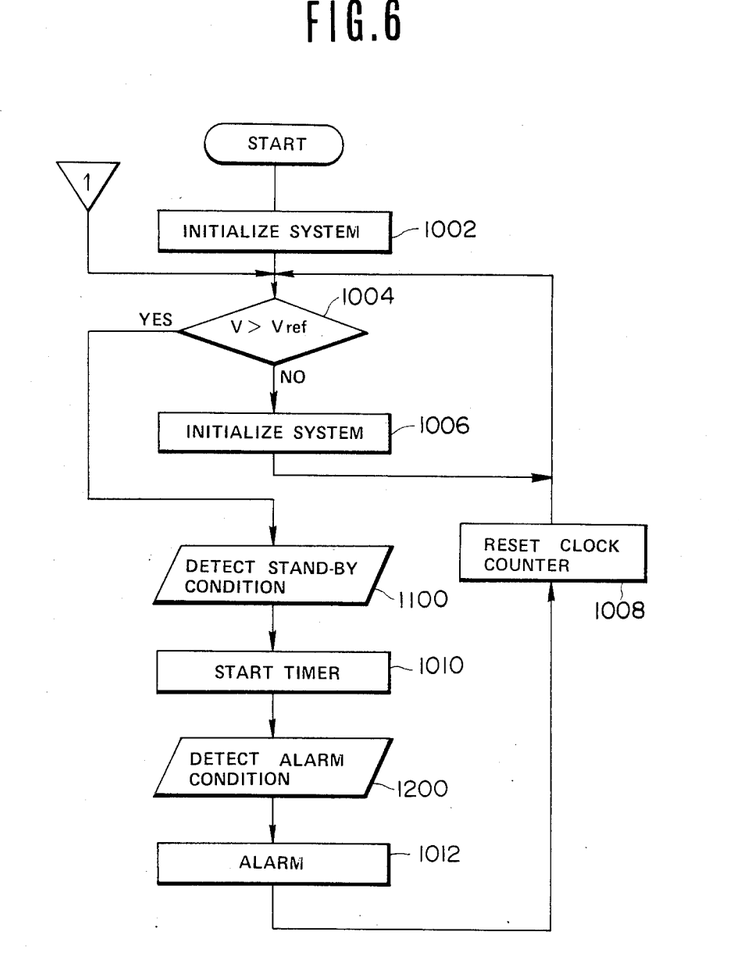
FIG. 6 is a flowchart of a main routine executed by the alarm system of FIG. 5.
Figure 7:
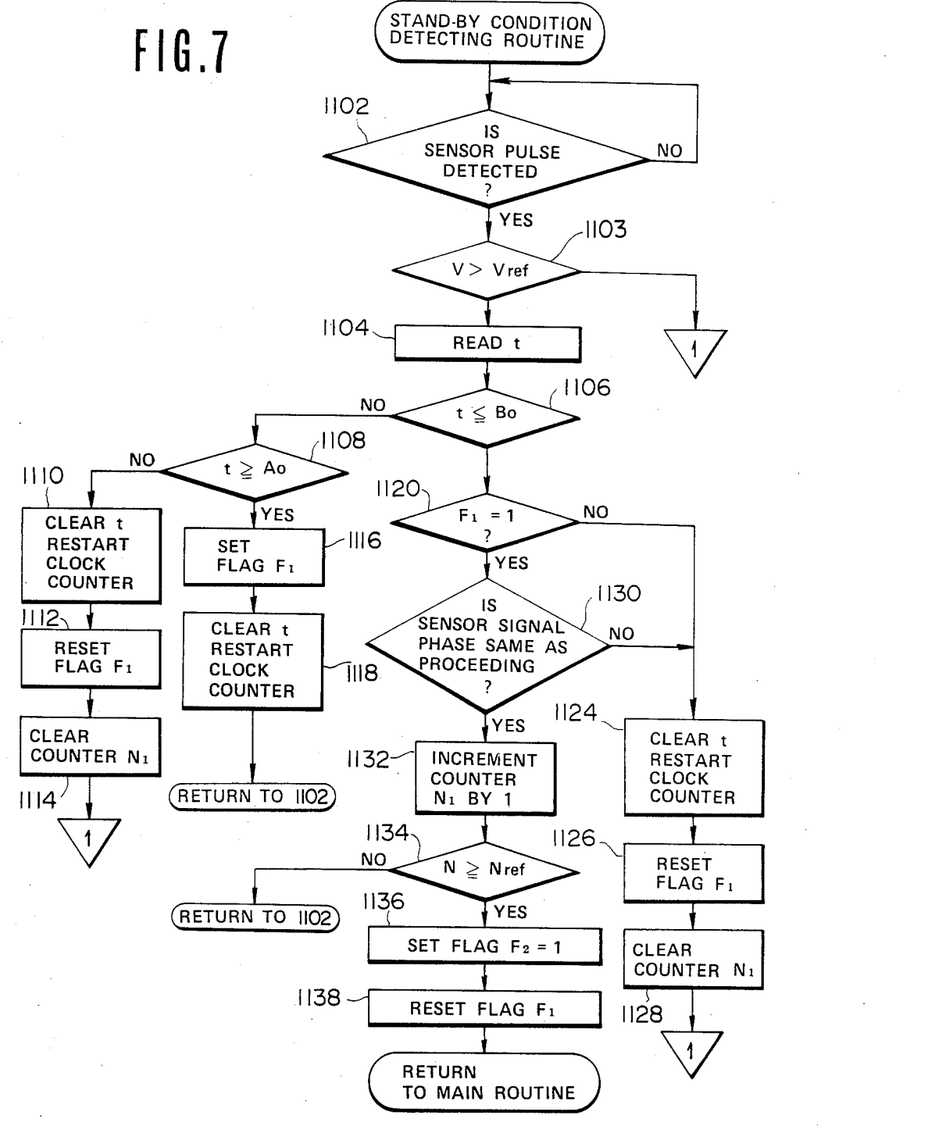
FIG. 7 is an alarm stand-by condition detecting sub-routine executed during execution of the main routine of FIG. 6.
Figure 8A:
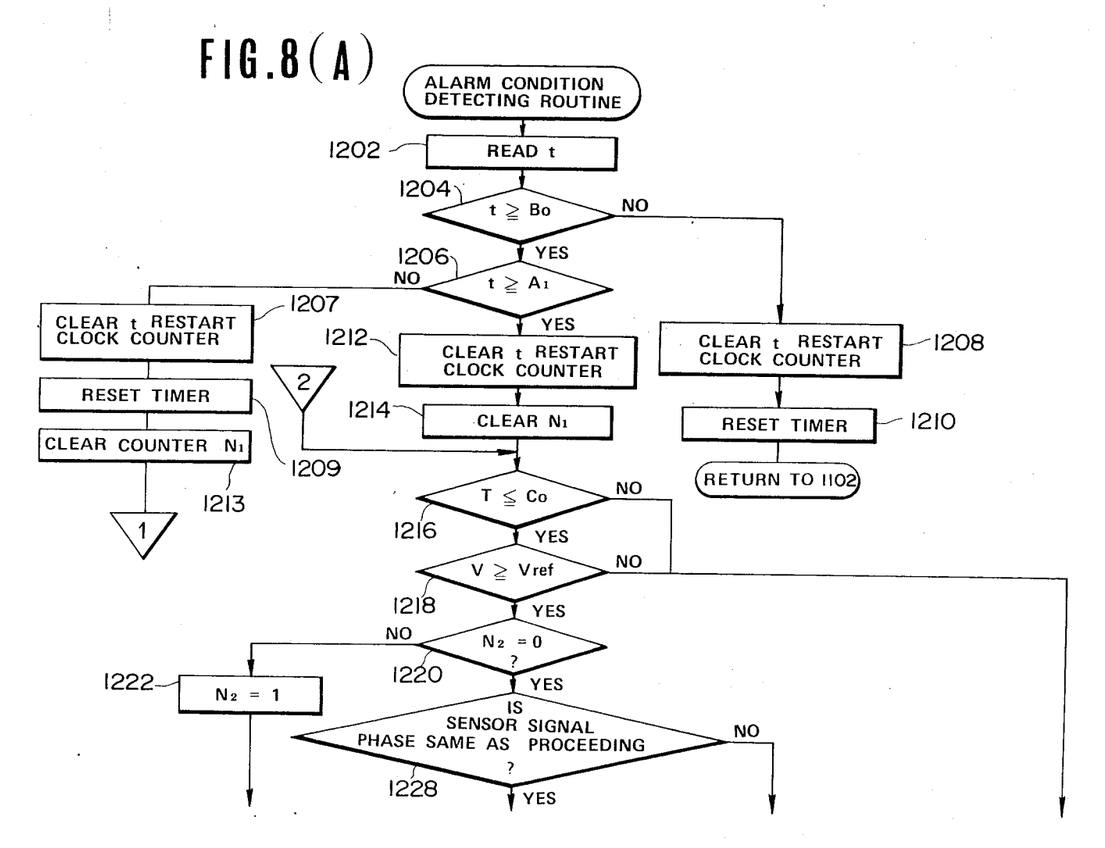
FIGS. 8(A) and 8(B) are together form a flowchart of an alarm condition detecting sub-routine executed during execution of the main routine of FIG. 6.
Figure 8B:
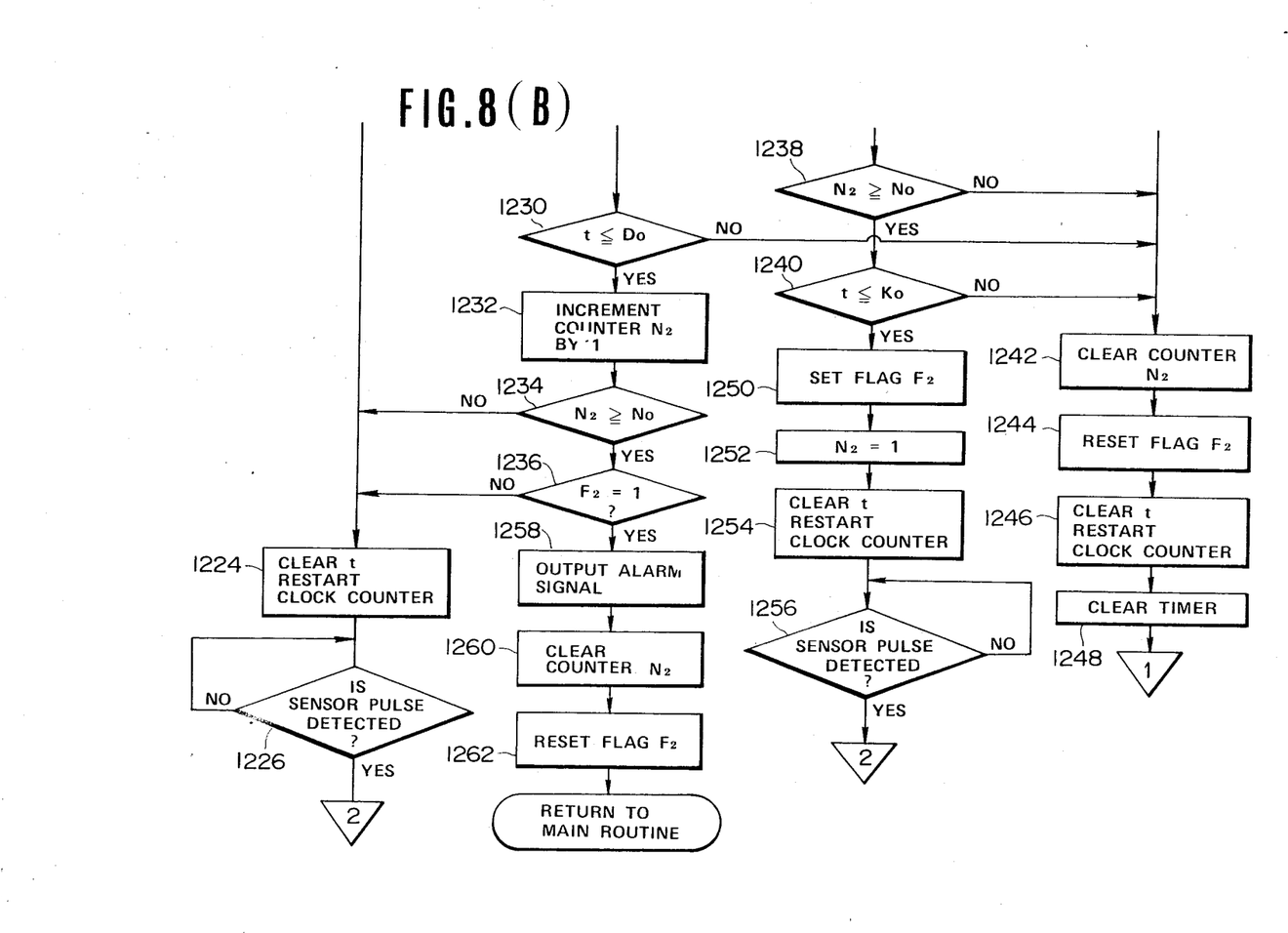

The operation of the second embodiment of the alarm system and method will be decribed below with reference to FIGS. 6 to 8 in which the flowchart of FIG. 6 illustrates a main program to be executed as a background job, the flowchart shown in FIG. 7 illustrates a sub-routine for detecting the stand-by state or condition, and the flowchart shown in FIG. 8 illustrates a sub-routine for detecting the alarm condition.

In the main program of FIG. 6, the system is initialized immediately after starting to execute, at a block 1002. The vehicle speed-indicative signal value V is read out and compared with the vehicle speed threshold $V_{ref}$, at a block 1004. If the vehicle speed is lower than the predetermined minimum speed represented by the vehicle speed threshold $V_{ref}$, the alarm system is again initialized at a block 1006 and control returns to the block 1004. Therefore, the blocks 1004 and 1006 form a waiting loop which executes until the vehicle speed exceeds the predetermined minimum vehicle speed.

When the vehicle speed indicative signal value V becomes greater than the vehicle speed threshold at the block 1004, the CPU begins to execute the stand-by condition detecting sub-routine of FIG. 7, at a block 1100. When the stand-by condition is satisfied and the driving condition satisfying the stand-by condition is detected during execution of the sub-routine of FIG. 7, process goes to a block 1010 to start a timer 60 of FIG. 5 which feeds a timer signal indicative of elapsed time from initiation of the stand-by condition. Thereafter, the alarm condition detecting sub-routine of FIG. 8 is executed at a block 1200. When the alarm condition is satisfied during execution of the alarm condition detecting sub-routine, an alarm is issued at a block 1012. Then processing returns to the block 1400 via a re-initializing step at block 1008.

Now, the stand-by condition detecting sub-routine will be described herebelow with reference to FIG. 7. First, the stand-by condition detecting sub-routine waits for a steering angle sensor pulse at a block 1102, which is repeated until the next steering angle sensor pulse is received. During the period of time in which the block 1102 is repeated, the clock signal counting section 130 of the counter 128 counts the clock signal pulses from the clock generator 30 in order to measure the period of time during which no steering angle sensor pulses are received. When a steering angle sensor pulse is finally received at the block 1102, the vehicle speed-indicative signal value V is again checked at a block 1103. If the vehicle speed-indicative signal value V is less than the vehicle speed threshold $V_{ref}$ at the block 1103, control returns to the main-routine at MERGE 1 which leads back to block 1004. On the other hand, when the vehicle speed indicative signal value V is still greater than the vehicle speed threshold $V_{ref}$, the block signal counter section 130 of the counter 128 is accessed to retrieve the counter value t thereof, at a block 1104. The counter value t read at the block 1104 is compared with the first timer threshold $B_0$ at a block 1106.

If the counter value t is greater than the first timer threshold $B_0$, the counter value t is further compared with the first monotonous threshold $A_0$ at a block 1108. If the counter value t is equal to or less than the first monotonous threshold $A_0$, the clock signal counter section 130 is reset to clear the counter value t and restart the counting operation of the clock signal, at a block 1110. The memory section 138 of the register which serves as a monotonous state flag $F_1$, indicative of whether or not the monotonous criterion of the stand-by condition is satisfied, is reset, at a block 1112. Then, the counter section 132 for counting the steering angle sensor pulses is reset to clear its counter value $N_1$, at a block 1114. Thereafter, the control returns to the main program at MERGE 1.

When the counter value t of the clock signal counting section 130 of the counter 128 is greater than the first monotonous threshold $A_0$ when checked at the block 1108, the monotonous state flag $F_1$ in the memory section 138 of the register 136 is set. Thereafter, the counter value t of the clock signal counting section 130 is cleared and the counting operation is restarted, at a block 1118. Then, control returns to the block 1102 to wait for the next steering angle sensor pulse.

If the counter value t is equal to or less than the first timer threshold $B_0$ when checked at the block 1106, the monotonous state flag $F_1$ is checked at a block 1122. If the monotonous state flag is not set ($F_1=0$), the counter value t is cleared and the counter section is restarted at a block 1124. The monotonous flag $F_1$ is reset at a block 1126 and the counter value $N_1$ in the counter section 132 is then cleared at a block 1128. After the block 1128, control returns to the main program at MERGE 1.

When the monotonous state flag $F_1$ is set when checked at the block 1122, the signal phase of the sensor pulse is checked at a block 1130 for whether the steering adjustment causing the current steering angle sensor pulse was in the same direction as that causing the preceding steering angle sensor signal. If the sensor pulse phase is opposite that of the preceding one when checked at the block 1130, then control goes to the block 1124. On the other hand, when the signal phases of the last two sensor pulse signals are the same, the counter value $N_1$ in the memory section 138 of the counter 136 is incremented by 1, at a block 1132. The counter value $N_1$ is then compared with the angular threshold $N_{ref}$ at a block 1134. When the counter value $N_1$ is less than the angular threshold $N_{ref}$, process returns to the block 1102 to await the next sensor pulse.

When the counter value $N_1$ is equal to or greater than the angular threshold $N_{ref}$ when checked at the block 1134, a stand-by state flag $F_2$ is set in the memory section 140 of the register 136 at a block 1136 and thereafter the monotonous state flag $F_1$ is reset at a block 1136 and thereafter the monotonous state flag $F_1$ is reset at a block 1138. After the block 1138, control returns to the main program at the block 1010 to start the timer 60.

In the alarm condition detecting sub-routine of FIG. 8 which is executed after the block 1010, the counter value t of the clock signal counting section 130 of the counter 128 is again read out at a block 1202. At a block 1204, the counter value t is compared with the first timer threshold $B_0$. If the counter value t is equal to or less than the first timer threshold $B_0$, the counter value t is cleared and the counting of the clock signal is restarted at a block 1208. Thereafter, the timer 60 is reset at a block 1210. Finally, control returns to the block 1102 of the stand-by state detecting sub-routine.

When the counter value t is greater than the first timer threshold $B_0$, the counter value t is further compared with a second monotonous state threshold $A_1$, at a block 1206. When the counter value t is less than the second monotonous state threshold $A_1$, the counter value t is cleared and counting of the clock signal is restarted at a block 1207. Thereafter, the timer is reset at a block 1209, and the counter value $N_1$ is cleared at a block 1213. Thereafter, control returns to the main program at MERGE 1.

When the counter value t is equal to or greater than the second monotonous state threshold $A_1$ at block 1206, the counter value t is cleared and counting of the clock signal is restarted at a block 1212. The counter value $N_1$ is also cleared at a block 1214. After this, the timer signal value T of timer 60 is compared with a timeover threshold $C_0$ which defines the maximum duration of the stand-by condition before the alarm system is reset to its initial state. When the timer signal value T is less than the time over threshold $C_0$ when checked at the block 1216, the vehicle speed-indicative signal V is again checked to ensure that it is equal to or greater than the vehicle speed threshold $V_{ref}$.

If the vehicle speed indicative signal value V is equal to or greater than the vehicle speed threshold $V_{ref}$, the counter value $N_2$ of a counting section 134 which counts the sensor pulses is checked at a block 1220. When the counter value $N_2$ is zero, the counting section 134 is set to the value 1 at a block 1222. After resetting the value of the clock signal counting the next steering pulse is awaited at a block 1226. As in the foregoing block 1102, the block 1226 is repeated until the next sensor pulse is received. After the next sensor pulse is detected at a block 1226, control returns to MERGE 2 which leads back to step 1216.

When the counter value $N_2$ is non-zero when checked at the block 1220, then the signal phase of the sensor pulse is checked as in the foregoing block 1130. If the signal phase of the current sensor pulse is the same as that of the preceding pulse, the counter value t of the clock signal counting section 130 is compared with the second timer threshold $D_0$ at a block 1230. When the counter value t is less than the second timer threshold $D_0$, the counter value $N_2$ is incremented by 1 at a block 1232. Thereafter, the counter value $N_2$ is compared with an alarm threshold $N_0$ at a block 1234. If the counter value $N_2$ is less than the alarm threshold $N_0$, control goes to the block 1226 to detect the next sensor pulse via step 1224. On the other hand, when the counter value $N_2$ is equal to or greater than the alarm threshold $N_0$, a reverse steer flag $F_2$ in the memory section 140 of the register 136 is checked, at a block 1236. The reverse steer flag $F_2$, when set, indicates that the steering wheel was reversed after the steering adjustment resulting in the stand-by condition and this reversed adjustment is sufficiently large. When the reverse steer flag $F_2$ is not set at block 1236, control goes to the block 1226 via block 1224.

If reversal of the steering direction occurs and thereby the different phase of the sensor pulse is detected at the block 1228, the counter value $N_2$ is compared with the alarm threshold $N_0$ at a block 1238. When the counter value $N_2$ is equal to or greater than the alarm threshold $N_0$, then the counter value t of the clock signal counting section 130 is compared with a third timer threshold $K_0$ at a block 1240. When the counter value t is less than the third timer threshold $K_0$, the reverse steer flag $F_2$ is set at a block 1250 and the counter section 134 in the counter 128 is set to 1 at a block 1252. Thereafter, the counter value t is cleared and the counting of the clock signal is restarted at a block 1254. Subsequently, the next sensor pulse is awaited at a block 1256. The block 1256 is repeated until the next sensor pulse is detected. When the next sensor pulse is received at the block 1256, control returns to MERGE 2.

If at the block 1218 the vehicle speed-indicative signal value V is less than the vehicle speed threshold $V_{ref}$, or at the block 1238 the counter value $N_2$ is less than the alarm threshold $N_0$, or at the block 1230 the counter value t is greater than the second timer threshold $D_0$ or at the block 1240 the counter value t is greater than the third timer threshold $K_0$, control goes to a block 1242 to clear the counter value $N_2$. Thereafter, the reverse steer flag $F_2$ is reset at a block 1244, the clock signal counting section 130 is reset to clear the counter value and restart at a block 1246, and the timer is cleared at a block 1248. Then, control returns to the main program at MERGE 1.

When the steering direction is reversed after the steering adjustment in the previous direction exceeds the foregoing alarm threshold, and thus the reverse steer flag has been set at the block 1250, and when the counter value $N_2$ when checked at the block 1234 is equal to or greater than the alarm threshold $N_0$, the alarm signal is output at a block 1258. After this, the counter section 134 of the counter is cleared at a block 1260 and the reverse steer flag $F_2$ is reset at a block 1262. After the block 1262, control returns to the main program to produce an alarm at the block 1012. Thereafter, the clock signal counting section 130 is cleared or reset at a block 1008 and control returns to the block 1004.

As will be appreciated from the aforementioned alarm controller operation, in the shown embodiment, the alarm controller is responsive to consecutive, adequately extensive steering adjustments in opposite directions within a given time after the stand-by condition is satisfied to produce an alarm. Though the shown embodiment anticipates a monotonous state longer than the second monotonous threshold after the stand-by condition is satisfied before producing an alarm, this is not always necessary. Further, any of the alarm conditions disclosed in the co-pending U.S. patent application Ser. Nos. 304,254 (corresponding to EPO Publication No. 0048492), 309,012 (corresponding to EPO Publication No. 0049522), 326,392 (corresponding to Published Japanese Patent Application No. 56-2225), 326,393 (corresponding to Published Japanese Patent Application No. 56-2226), 377,267 (corresponding to the EPO Publication No. 0059225), 377,268 (corresponding to the EPO Publication No. 0060306), 377,198 (corresponding to the EPO Publication 0061501), and 377,206 (corresponding to the EPO Publication No. 0061500); can be applied. Therefore, the present invention should not be interpreted to apply only to the specific alarm conditions set forth above.

What is claimed is:

1. An alarm system for a drowsy vehicle driver comprising:
   a first detector for measuring a first period of time in which vehicle steering is substantially absent, said first detector being responsive to a first period of time longer than a first threshold to produce a first detector signal;
   a second detector for detecting a steering adjustment in a single direction, said second detector being responsive to steering adjustments through an angle exceeding a second threshold in the presence of said first detector signal to switch the alarm system to a stand-by state;
   a third detector for detecting a preselected steering operational condition while the system is in said stand-by state, and producing an alarm signal in response thereto; and an alarm means responsive to said alarm signal to produce an alarm to keep the driver awake.

2. The system as set forth in claim 1, wherein said second detector is responsive to steering adjustments in the direction opposite that of the last steering adjustment exceeding the second threshold to reset the system to its initial state.

3. The system as set forth in claim 2, which further comprises a timer for measuring a period of time for which the system is allowed to remain in said stand-by state and resetting the system to its initial state when the measured period of time exceeds a time-over threshold before said preselected steering operational condition is detected.

4. The system as set forth in claim 3, wherein said second detector also detects the rate of the steering adjustment and rests the system to its initial state when the detected adjustment rate is lower than a given rate.

5. The system as set forth in claim 4, wherein said third detector detects abrupt steering adjustments in opposite directions occurring within a given period of time, the angular extents of which exceeds a third threshold.

6. The system as set forth in claim 4, wherein said third detector detects abrupt steering operations in opposite directions within a given period of time after a period of time exceeding a fourth threshold in which steering is substantially absent.

7. An alarm system for notifying vehicle driver of drowsiness comprising:

a first sensor for detecting steering adjustments and producing a first signal including a sensor pulse whenever the steering wheel angular position is adjusted through a given unit angle, said sensor signal being indicative of the direction in which the steering adjustment occurs;

a second detector for measuring the period of time between consecutive sensor pulses and producing a second signal indicative of the measured period of time, a third detector responsive to said second signals having a value exceeding a first threshold to produce a third signal;

a fourth detector for counting first signals indicative of steering adjustment in the same direction and separated in time by less than a second threshold, said fourth detector producing a fourth signal to switch the system to a stand-by state when its counter value exceeds a third threshold;

a fifth detector for detecting a steering operation satisfying a predetermined alarm condition in the presence of said fourth signal to produce an alarm signal; and an alarm means, responsive to said alarm signal, for producing an alarm to keep the vehicle driver awake.

8. The system as set forth in claim 7, which further comprises a timer means for measuring the period of time for which the system remains in said stand-by state, said timer means producing a reset signal which resets the system to its initial state when the measured period of time exceeds a fourth threshold before said steering operation satisfying said alarm condition is detected.

9. The system as set forth in claim 8, wherein said fourth detector is responsive to receipt of said first signal before its counter value reaches said third threshold to reset the system to its initial state.

10. The system as set forth in claim 9, wherein the phase of said first signal depends upon the direction of the steering adjustment.

11. The system as set forth in claim 10, wherein said fifth detector detects abrupt steering adjustments in both directions respectively exceeding a fourth threshold with a variation speed thereof being higher than a fifth threshold to produce said alarm signal.

12. An alarm system for a vehicle driver for producing an alarm in order to prevent the driver from dozing at the wheel, comprising:

a first detector detecting steering adjustments through an angle exceeding a first threshold and producing a first signal when the steering adjustment is performed in a first direction and a second signal when the steering adjustment is performed in a second direction opposite said first direction, said first detector producing one of said first and second signals whenever the angle of adjustment of the steering wheel exceeds said first threshold;

a second detector receiving said first and second signals, measuring intervals between consecutive first and/or second signals to produce an interval-indicative signal indicative of the measured intervals;

a third detector which produces a third signal when the interval-indicative signal value exceeds a second threshold;

a fourth detector responsive to the interval-indicative signal value being less than a third threshold by counting occurrences of one of said first and second signals as long as the intervals between consecutive occurrences of said one of said first and second signals remain less than said third threshold, said fourth detector comparing its counter value with a fourth threshold and producing a fourth signal indicating a stand-by state when the counter value exceeds said fourth threshold in the presence of said third signal;

a fifth detector which produces an alarm signal when a steering operational condition satisfies a predetermined alarm condition in the presence of said stand-by state indicated by said fourth signal; and means for producing an alarm in response to said alarm signal.

13. The system as set forth in claim 12, which further comprises a timer associated with said fifth detector for measuring the duration of said stand-by state indicated by said fourth signal and resetting the system when the measured duration of said stand-by state exceeds a time-over threshold before the occurrence of said steering operational condition satisfying said alarm condition.

14. The system as set forth in claim 13, wherein said fourth detector is responsive to an interval between occurrences of said one of first and second signals in excess of said third threshold by resetting the system to an initial state thereof.

15. The system as set forth in claim 13, wherein said fourth detector is responsive to occurrences of the other of said first and second signals before its counter value reaches said fourth threshold by resetting the system to an initial state thereof.

16. The system as set forth in claim 13, wherein said fourth detector produces a reset signal which resets the system to an initial state thereof when the interval-indicative signal value is greater than said third threshold or the other of said first and second signals is received before the counter value reaches said fourth threshold.

17. The system as set forth in claim 12, wherein said stand-by state indicated by said fourth signal has a predetermined duration corresponding to a time-over threshold.

18. A method for detecting the drowsiness of a vehicle driver comprising the steps of:
   detecting occurrences of steering adjustments to detect intervals between occurrences in excess of a first given threshold;
   detecting occurrences of steering adjustments through angles exceeding a second threshold within a given period of time after the occurrence of intervals exceeding said first given threshold thereby initiating a stand-by state;
   detecting a specific steering operation in said stand-by state within a period of time less than a third threshold after initiation of said stand-by state; and
   producing an alarm in response to said specific steering operation occurring after the steering adjustment exceeding said second threshold, whereby a steering adjustment alarm is produced in response to occurrence of said specific steering operation within said third threshold from initiation of a stand-by state.

19. The method as set forth in claim 18, wherein the step of detecting the steering adjustment exceeding said second threshold is performed on consecutive steering adjustments in a single steering direction.

20. The method as set forth in claim 19, wherein the step of detecting the steering adjustments exceeding said second threshold is terminated when a steering adjustment in the direction opposite said single direction is detected before the steering adjustment in said single direction exceeds said second threshold.

21. The method as set forth in claim 20, which further comprises the step of detecting the rate of steering adjustment while carrying out the step of detecting the steering adjustment exceeding said second threshold, and terminating said detection of the steering adjustment when the detected steering adjustment rate is slower than a given rate.

22. The method as set forth in claim 21, wherein in the step of detecting said specific steering operation, abrupt steering adjustments in opposite directions alternatingly are detected.

23. A method for detecting the drowsiness of a vehicle driver comprising the steps of:
   detecting occurrences of steering adjustments to detect intervals between occurrences in excess of a first given threshold;
   detecting occurrences of steering adjustments through angles exceeding a second threshold within a given period of time after the occurrence of intervals exceeding said first given threshold thereby initiating a stand-by state;
   detecting a specific steering operation in said stand-by state; and
   producing an alarm in response to said specific steering operation occurring after the steering adjustment exceeding said second threshold, whereby a steering adjustment alarm is produced in response to occurrence of said specific steering operation within said third threshold from initiation of a stand-by state.

24. A method as recited in claim 23 wherein said step of detecting occurrences of steering adjustments to detect intervals between occurrences in excess of said first given threshold includes the further step of awaiting a determination that vehicle speed exceeds a predetermined threshold therefor.

* * * * *